United States Patent [19]

Kaji et al.

[11] Patent Number: 5,559,283
[45] Date of Patent: Sep. 24, 1996

[54] CASING STRUCTURE FOR CHROMATOGRAPH

[75] Inventors: Hironori Kaji, Katsuta; Atushi Ninomiya, Oume; Isamu Takekoshi, Edogawa-ku; Hideo Seki, Naka-gun; Kaoru Hagiya, Hitachi, all of Japan

[73] Assignee: Hitachi, Ltd., Tokyo, Japan

[21] Appl. No.: 309,695

[22] Filed: Sep. 21, 1994

[30] Foreign Application Priority Data

Oct. 5, 1993 [JP] Japan .................. 5-249336

[51] Int. Cl.⁶ ........................... G01N 30/54
[52] U.S. Cl. .................. 73/61.56; 96/106; 73/431
[58] Field of Search ............. 73/23.41, 23.42, 73/61.56, 431; 96/106; 95/82; 285/93, 121

[56] References Cited

U.S. PATENT DOCUMENTS

| | | | |
|---|---|---|---|
| 3,053,077 | 9/1962 | Tracht | 96/106 |
| 4,597,291 | 7/1986 | Motomiya | 73/431 |
| 5,131,272 | 7/1992 | Minei et al. | 73/431 |
| 5,298,225 | 3/1994 | Higdon | 73/23.42 |

FOREIGN PATENT DOCUMENTS

| | | |
|---|---|---|
| 61-189264 | 11/1986 | Japan . |
| 735290 | 2/1988 | Japan . |

*Primary Examiner*—Robert Raevis
*Attorney, Agent, or Firm*—Kenyon & Kenyon

[57] ABSTRACT

A casing structure for chromatograph having a plurality of casings respectively installing at least a separating column, a sample inducing portion and/or a detector portion of the chromatograph and the casings are vertically stacked one on another or horizontally juxtaposed one to another. The casing structure further comprises a passage for installing reagent feed pipes therein, and the passage is respectively provided in respective side portions of the casing for communicating with that of another casing when in the stacked state or in the juxtaposed state, and has an inner hole at an inner side thereof for connecting the reagent feed pipes to a pipe connecting portion arranged in the casings, and the passage has a cover at an outer side thereof for being opened outside of the casing.

13 Claims, 14 Drawing Sheets

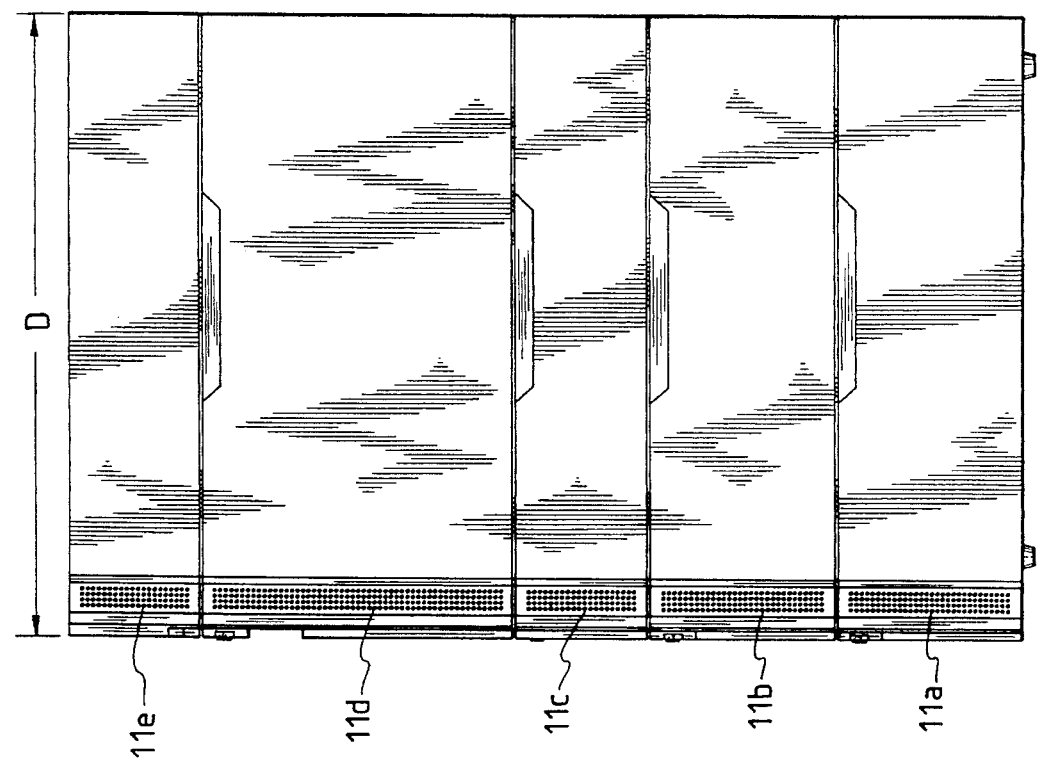
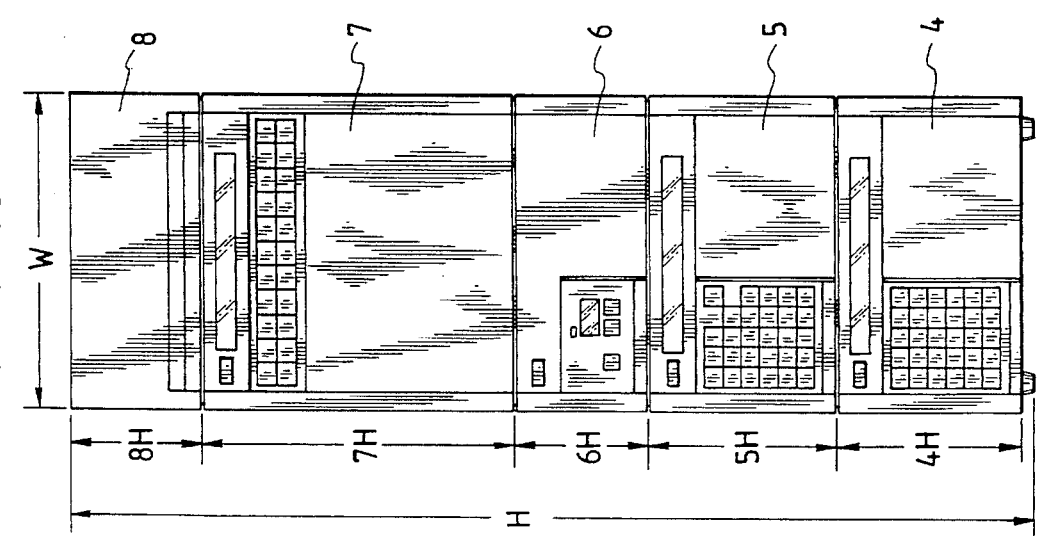

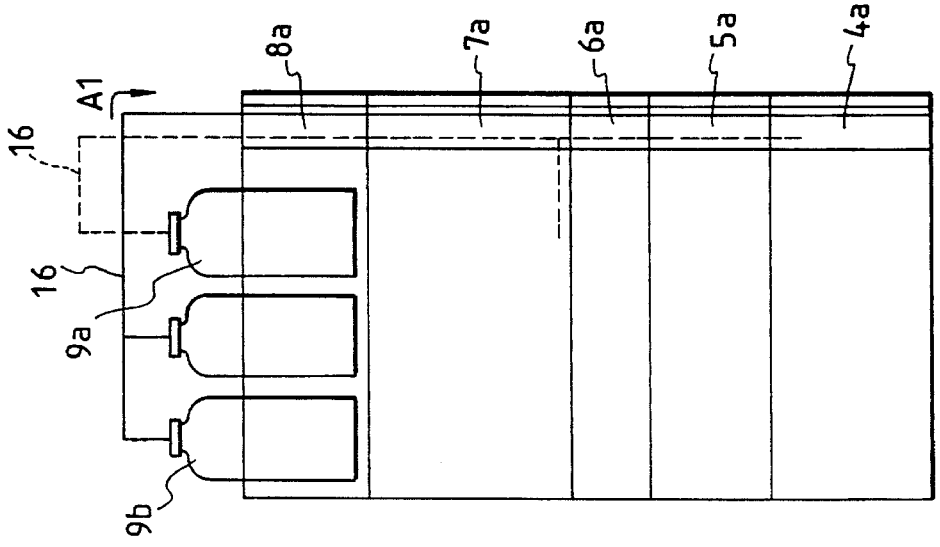
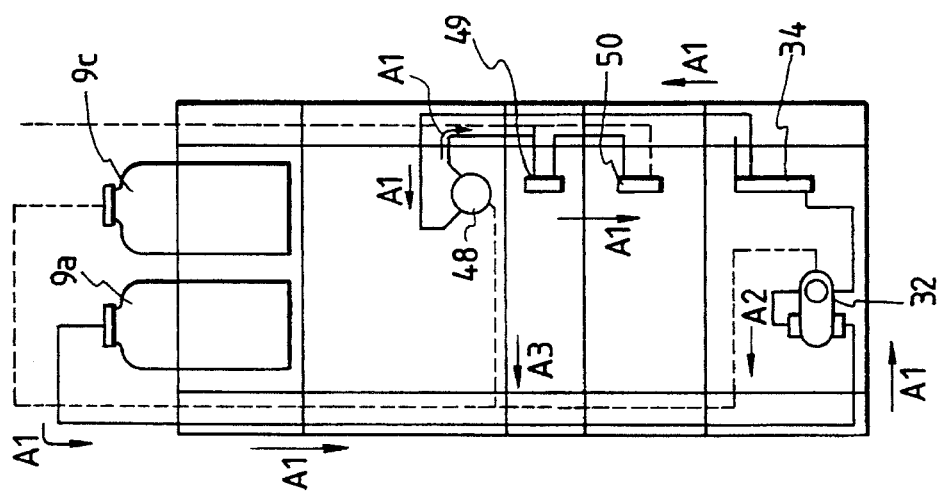
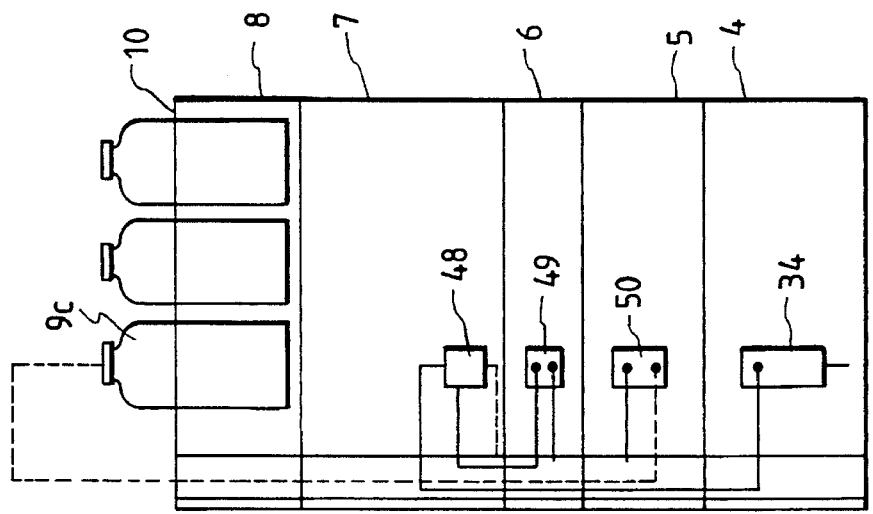

CASING STRUCTURE FOR CHROMATOGRAPH

BACKGROUND OF THE INVENTION

The present invention relates to a casing structure for chromatograph and, more particularly, to a casing structure for a separating analyzer such as a liquid chromatograph or a gas chromatograph for separating a mixture sample and for qualitative and quantitative analyses of the separated individual ingredients.

In the liquid or gas chromatograph of the prior art, the individual units are casings which are so functionally separated that they can be stacked.

As the aforementioned casing structure, there has been proposed a portable gas chromatograph in which a carrier gas container unit, a column unit, a column heating unit, a sample gas injection unit and a data display unit which all have outer faces with an identical shape so that they are stacked one on another to improve the design and production efficiencies and to reduce the production cost. In connection with this, there has been disclosed the technology of Japanese Utility Model Laid-Open No. 61-189264(1986).

In Japanese Design Registration No. 735290, moreover, there is disclosed the technology in which an eluent feeder for a liquid chromatograph is combined with another stackable unit such that the individual units are connected through a plurality of eluent feed pipes. In connection with this, there has also been disclosed the technology of Japanese Design Registration No. 735290.

In the liquid or gas chromatograph of the prior art, the casings are set separate and independent of each other for the individual functions of the units. Thus, for the separating analyzer to exhibit its functions, the individual casings for the units have to be connected to each other through the power supply cords for supplying the electric power; the signal lines for transmitting electric signals; and reagent feed pipes for feeding gases, sample liquids, reagents and cleaning fluids.

Usually, the connecting portions disposed at the back faces of the individual casings are connected through the power supply cords and the signal lines, and the reagent feed pipes are connected through the connecting portions disposed at the front faces of the individual casings.

As a result, the power supply cords, the signal lines and the reagent feed pipes are wired or piped while being exposed from the outer faces of the casings or by making use of the gaps between the casings, thereby causing problems in the appearance.

Moreover, some consideration is made for giving an identical shape to the upper faces of the individual casings so that they can be stacked. However, there is left unsolved a problem that the shapes, arrangement and/or constructions of the various switches at the front faces fail to provide an integral appearance.

Moreover, the separating analyzer of the prior art, which can be separately installed, is fixed by using a separate mounting frame or fitting, because the individual casings have to be vertically fixed for safety.

As a result, the mounting frame or fitting protrudes to the outside of a casing to endanger the operator as well as provide deteriorated appearance.

Especially in the casings for the separating analyzer of the prior art, which can be separately mounted, the reagent feed pipes and so on are arranged to meander through the gaps between the individual casings from one pipe connecting portion to another. As a result, there arises another problem that the piping distance is elongated thereby increasing the total amounts of reagents or cleaning fluid required and increasing the time for the setup and the cleaning operation.

Moreover, the amounts of liquids for the qualitative and quantitative analyses of the separated individual ingredients are increased to raise another problem that the accuracy for microanalysis of the mixture sample is adversely affected.

In addition, the reagent feed pipes and so on projecting to the outside of the individual casings are susceptible to breakage. This breakage will invite the loss of precious analysis data or the scatter of dangerous reagents being fed in the reagent feed pipes. Thus, a serious problem arises in the safety.

Moreover, the reagent feed pipes and so on are complicated and entangled. Thus, another problem is that the reagent feed pipes are difficult to confirm and maintain when they are installed or removed.

Still moreover, the separating analyzer to be separately installed is equipped on the bottom faces of its casings with legs so that the individual unit casings may be independently mounted to leave gaps to be accessed in the stacking operation.

However, the legs have to leave the gaps for the accesses at the stacking time, thus raising a problem that they deteriorate the integral appearance of the entire analyzer and increase the total height.

SUMMARY OF THE INVENTION

The present invention has been conceived to solve the above-specified problems of the prior art and to provide a space-saving-type separating analyzer which is enabled to have its component casings either vertically stacked or horizontally juxtaposed and separately arranged by giving substantially the same shape to the outer faces of the casings. The present invention can have the distance of its reagent feed pipes or the like minimized. The present invention is safe and has excellent appearance and an integral exterior.

To achieve the above-specified object, according to the present invention, there is provided a separating analyzer comprising: a plurality of casings; a pump unit; and a detector unit, wherein the casings are made to have a substantially identical outer face shape so that they can be vertically stacked one on another or horizontally juxtaposed one to another, and wherein each of the casings includes: a first passage communicating with that of another casing when in the stacked or juxtaposed state; and a second passage for connecting the first passage and a pipe connecting portion of each of members arranged in the casings.

Moreover, the casings are made to have a substantially identical upper face shape so that they can be vertically stacked one on another or horizontally juxtaposed one to another, and include first passages communicating with one another when in the stacked state or the juxtaposed state.

Each of the casings further includes: a plurality of protruding legs on the bottom face thereof; and a corresponding number of leg receiving portions recessed in the upper face thereof and positioned to correspond to the legs so that the legs can be fitted in the receiving portions.

Each of the casings further includes notches formed in at least either of the two side ends of the upper and lower faces thereof.

Further comprised are fixing plates for plugging the notches to fix the lower one of the casings, when the casings are stacked, and for exposing the notches to the outside to release the lower casing from its fixed state when the casings are separated.

There is further provided a separating analyzer comprising: a plurality of casings; a pump unit; and a detector unit, wherein the casings are made to have a substantially identical side face shape so that they can be horizontally juxtaposed one to another, and include first passages communicating with one another when in the stacked state.

Each of the casings has a fixing portion in the first passage thereof for fixing the casings to each other. The first passages are formed by forming recessed grooves in the outer faces of the casings. Each of the casings further includes a cover capable of arbitrarily taking a state, in which it exposes the each casing to the outside, and a state in which it shields the same from the outside.

In case the casings are individually arranged with control switches, on the other hand, these control switches are concentrated in predetermined faces thereof, and the first passages are positioned in the vicinity of front edge portions of the remaining faces adjacent to the predetermined faces and at the back of the control boards of the control switches so that the first passages and the control boards are overlapped, as viewed from the predetermined faces.

Moreover, each of the casings further includes a front cover forming the casing front portion and having its outer face formed of a smoothened uniform surface, and each of the first passages has a cover for forming a flat surface on the outer face of the front cover when the front cover is closed.

Thus, according to the construction of the present invention, the casings are made to have a substantially identical outer face shape so that they can be vertically stacked one on another or horizontally juxtaposed one to another, and each of the casings includes: a first passage communicating with that of another casing when in the stacked or juxtaposed state; and a second passage for connecting the first passage and a pipe connecting portion of each of members arranged in the casings. As a result, the reagent feed pipes and so on between the individual casings can be piped through the first passages and the second passage without being exposed to the outside and at the shortest distance. Thus, it is possible to reduce the amounts of liquids in the reagent feed pipes and accordingly to reduce the total amounts of reagents and cleaning fluid to be fed. Therefore the time periods for the setup and the cleaning operation and are shortened the accuracy of microanalysis of the mixture samples is improved.

On the other hand, the individual casings are equipped on their bottom faces with the protruding legs and in the top faces with the recessed receiving portions which are positioned to correspond to the legs. As a result, when the legs are fitted in the receiving portions, the casings can be stacked stably without any cap while ensuring the communication of the first passages.

The casings are formed in at least the two side ends of their top and bottom faces with the notches, which can be manually handled to stack the casings with a reduced height while maintaining the separability thereby to provide an integral appearance.

Moreover, the fixing plates are provided for plugging the notches to fix the lower one of the casings, when the casings are stacked, and for exposing the notches to the outside to release the lower casing from its fixed state when the casings are separated. As a result, a better integral appearance can be established.

Each of the casings has the fixing portion in the first passage thereof for fixing the casings to each other so that the casings can be stably stacked or juxtaposed. The first passages are formed by forming the recessed grooves in the outer faces of the casings so that the reagent feed pipes and so on can be prevented from projecting from the outer faces of the casings. Each of the casings further includes the cover capable of arbitrarily taking a state, in which a relative first passage is exposed to the outside, and a state in which it is shielded from the outside. As a result, the reagent feed pipes and so on can be protected from any breakage against an external force. Thus, the safety can be improved to prevent the loss of precious analysis data or the scatter of dangerous reagents being fed in the reagent feed pipes.

Moreover, the casings are individually arranged to have their reagent feed pipes and so on concentrated along the first and second passages so that the pipes can be easily mounted and demounted. In case, on the other hand, the casings are individually arranged with control switches, these control switches are concentrated in predetermined faces thereof, and the first passages are positioned in the vicinity of front edge portions of the remaining faces adjacent to the predetermined faces and at the back of the control boards of the control switches so that the first passages and the control boards are overlapped. As a result, an integral appearance can be provided while saving the space.

Moreover, the front cover forms the casing front portion and its outer face is formed of a smoothened uniform surface; each of the first passages has a cover for forming a flat surface on the outer face of the front cover when the front cover is closed. As a result, the reagent feed pipes can be protected from any breakage by an external force, and the appearance can be made integral.

BRIEF DESCRIPTION OF THE DRAWINGS

FIG. 10A and 10B are dimensioned diagrams showing the liquid chromatograph body of FIG. 1.

FIG. 12A–C are explanatory diagrams showing the piping of the liquid chromatograph body of FIG. 1.

DETAILED DESCRIPTION

A separating analyzer according to the present invention will be described in the following in connection with its embodiments with reference to FIGS. 1 to 18.

Figure 1:
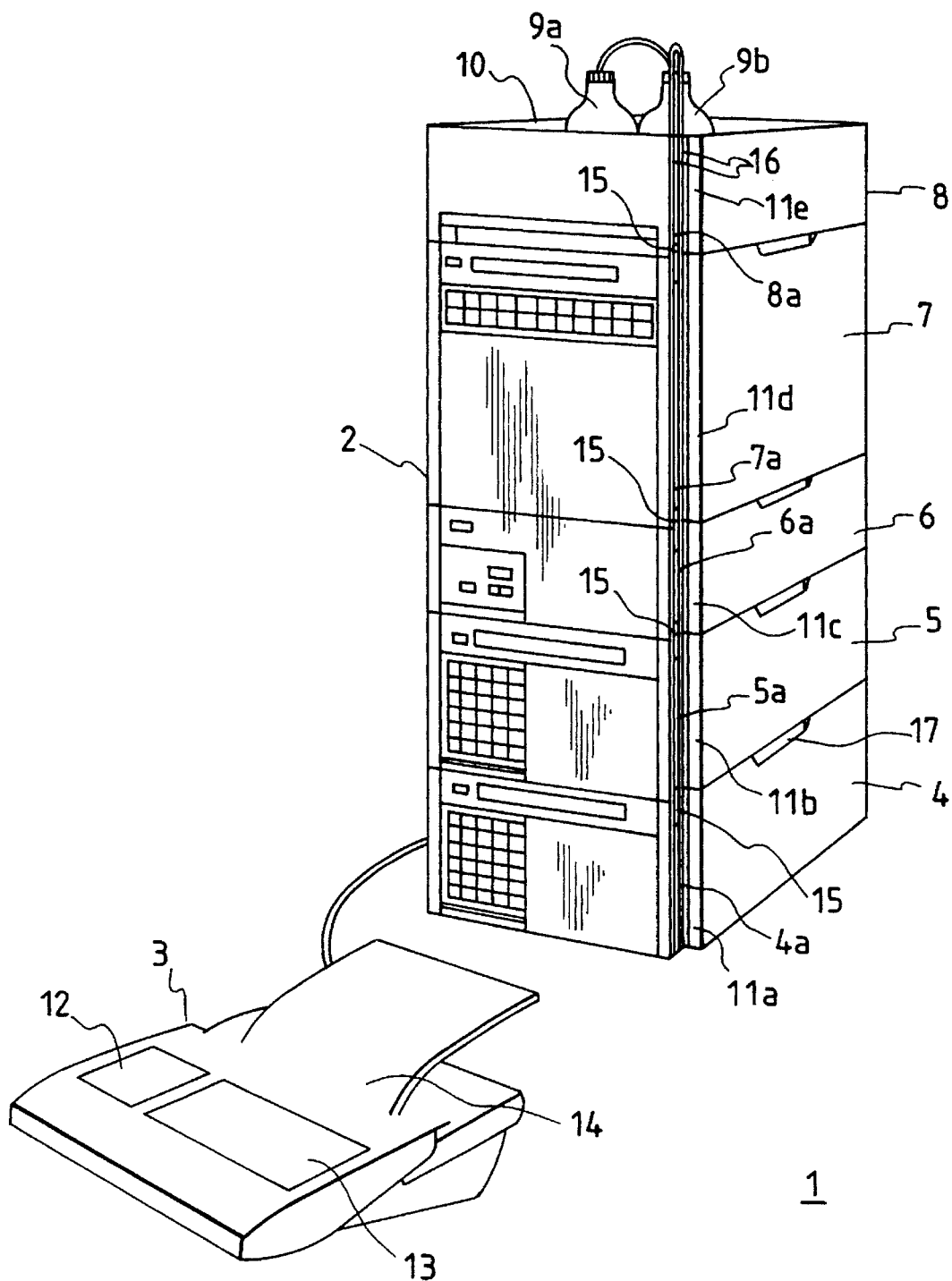
FIG. 1 is a perspective view showing the exterior of a liquid chromatograph according to one embodiment of a separating analyzer of the present invention.

A liquid chromatograph according to the first embodiment for the present invention will be described in connection with its casing with reference to FIGS. 1 to 13. FIG. 1 is a perspective view showing the exterior of a liquid chromatograph according to the first embodiment of a separating analyzer of the present invention.

In FIG. 1, reference numeral 1 designates a liquid chromatograph which is constructed to include a liquid chromatograph body 2 and a data processor 3 connected with the liquid chromatograph body 2 through connecting cords.

The liquid chromatograph body 2 is constructed of box-shaped casings 4, 5, 6, 7 and 8 which are functionally separated but given an identical top face shape so that they can be stacked one on another.

These casings 4 to 8, excluding the uppermost casing 8, can be so interchangeably stacked as to accommodate varying mixture samples to be separated and analyzed. Moreover, each of the casings 4 to 8 is formed in its two sides with first passages 4a to 8a which are so recessed that they can communicate with each other when the casings are stacked.

The first passages 4a to 8a are piped with liquid feeding pipes 16. Moreover, the casings 4 to 8 are fixed to one another through fittings 15 which are mounted on the first passages 4a to 8a.

In a manner to correspond to the first passages 4a to 8a, still moreover, there are provided covers 11a to 1e for covering the fittings 15 and the pipes 16.

On the other hand, the casings 4 to 7 are formed at the central portions of the two side end portions of their top faces with notches 17, which are used to hold the individual casings 4 to 8 when these casings are to be stacked or separated.

In the present embodiment: the casing 4 arranged in the lowermost position is used as a pump unit; the casing 5 arranged on the casing 4 is used as a detector unit; the casing 6 arranged on the casing 5 is used as a column oven unit; the casing 7 arranged on the casing 6 is used as a sample feed unit; and the casing in the uppermost position is used as a reservoir unit.

This casing 8 acting as the reservoir unit is equipped with a reagent container 10 for accommodating a bottle 9a for an eluent and a bottle 9b for a cleaning fluid.

The casing 4 acting as the pump unit 4 pumps without pulsations the liquids from the bottles 9a and 9b of the casing 8 or the reservoir unit to the sample feed unit of the casing 7.

This sample feed unit of the casing 7 dispenses the liquids delivered from the pump unit of the casing 4 to a plurality of samples for dilution or addition.

The column oven unit of the casing 6 separates the individual ingredients by moving the analyzing eluent from the sample feed unit of the casing 7 through columns disposed therein.

The detector unit of the casing 5 analyzes the separated ingredients coming from the column oven unit of the casing 6 to output analysis data signals to the data processor 3.

This data processor 3 has a controller and a memory packaged therein for receiving the analysis data from the analyzer body 2 through connecting cords to analyze them, and is equipped with a display 12, an input unit 13 and a printer 14.

The data processor 3 records and computes the analysis data to prepare and output the graphs of various analysis data to the display 12 and the printer 14.

Here will be described the detailed structure of the pump unit of the casing 4.

Figure 2:
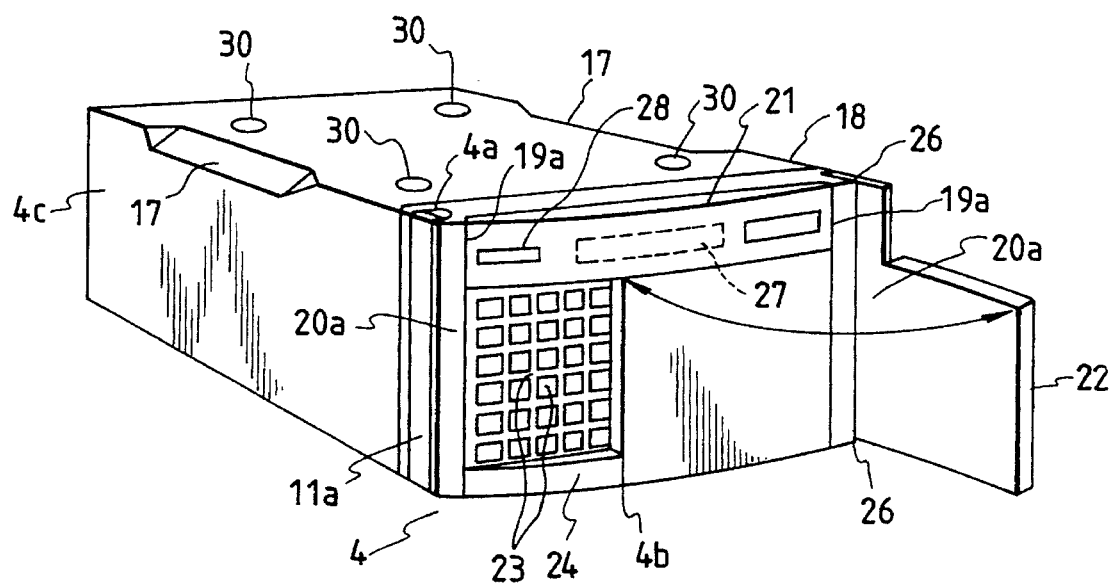
FIG. 2 is an enlarged explanatory view showing a pump unit constituting the liquid chromatograph of FIG. 1.
Figure 3:
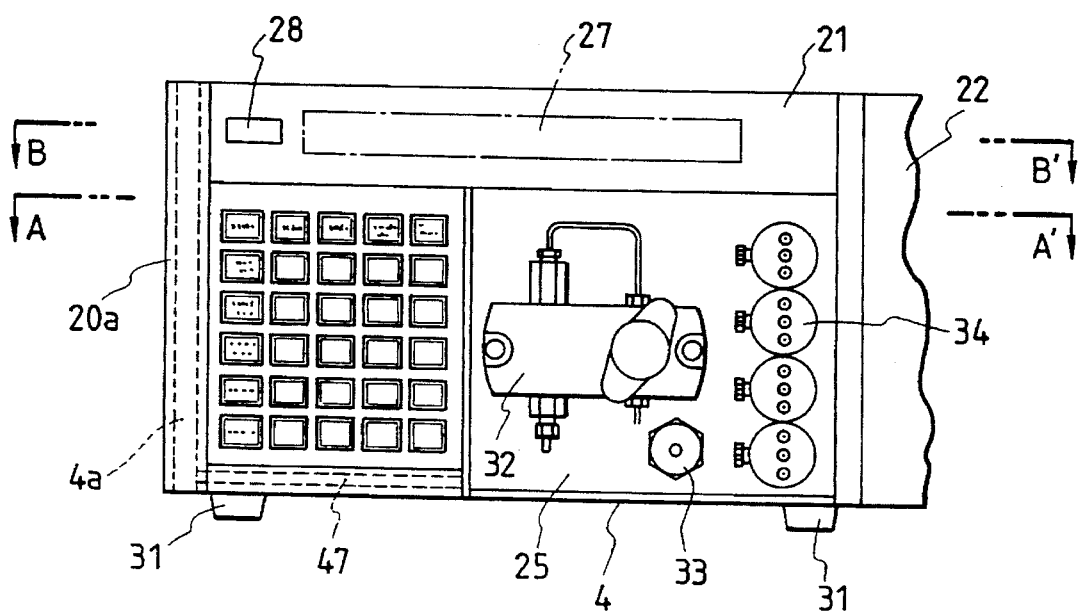
FIG. 3 is a front elevation showing the pump unit constituting the liquid chromatograph of FIG. 1.
Figure 4:
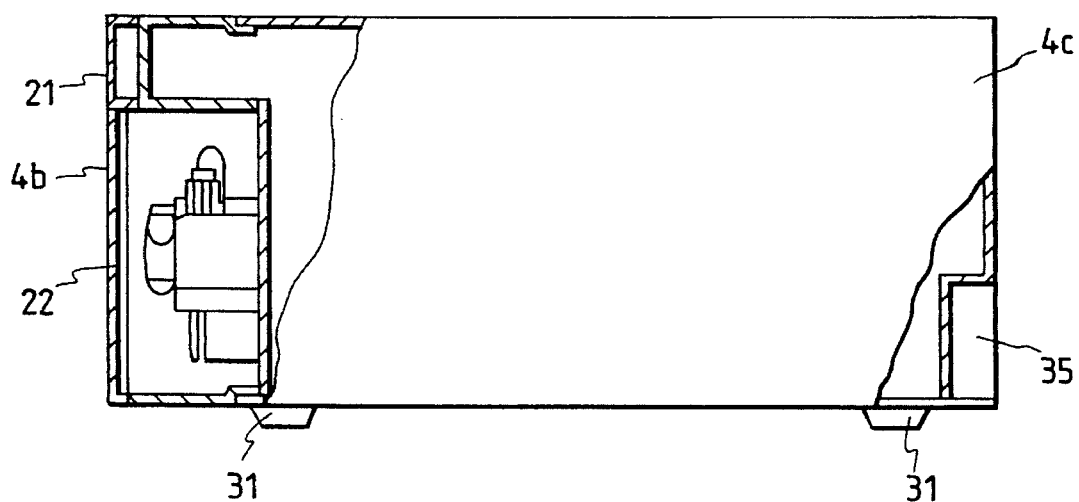
FIG. 4 is a partially sectional righthand side elevation showing the pump unit constituting the liquid chromatograph of FIG. 1.
Figure 5:
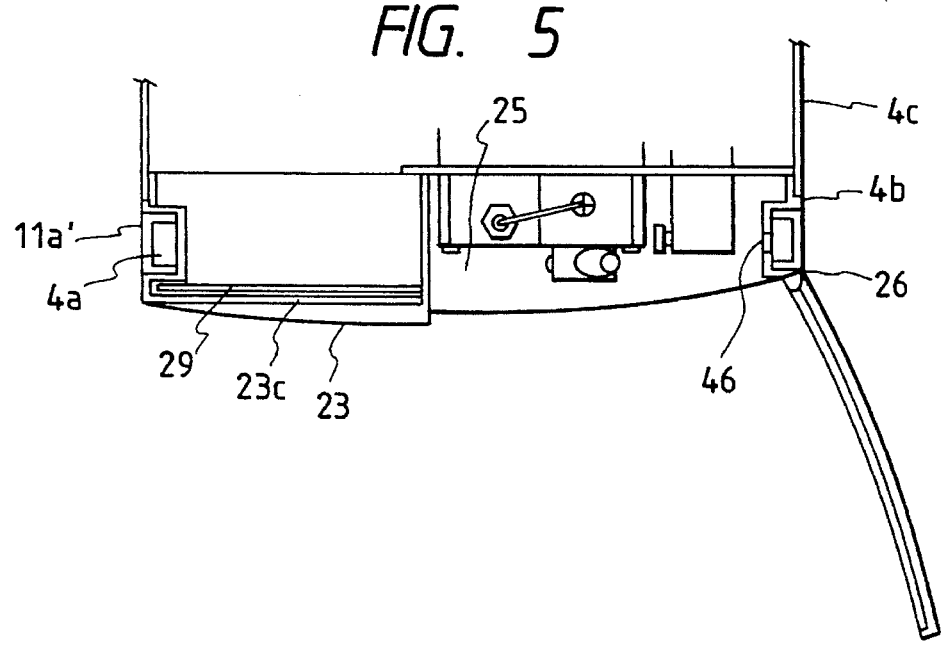
FIG. 5 is a section of the casing and the pump unit as taken along line A—A of FIG. 3.
Figure 6:
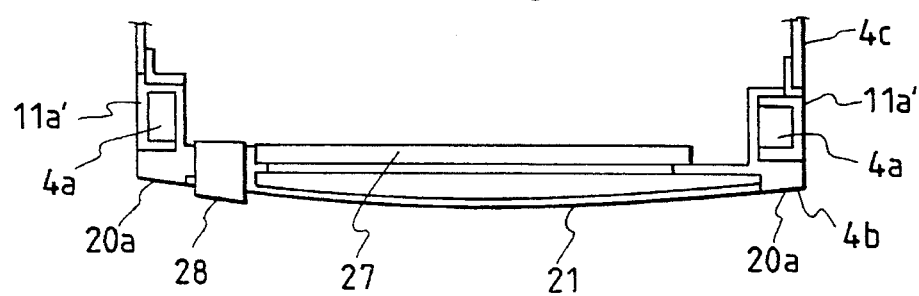
FIG. 6 is a section of the casing and the pump unit as taken along line B—B of FIG. 3.
Figure 7:
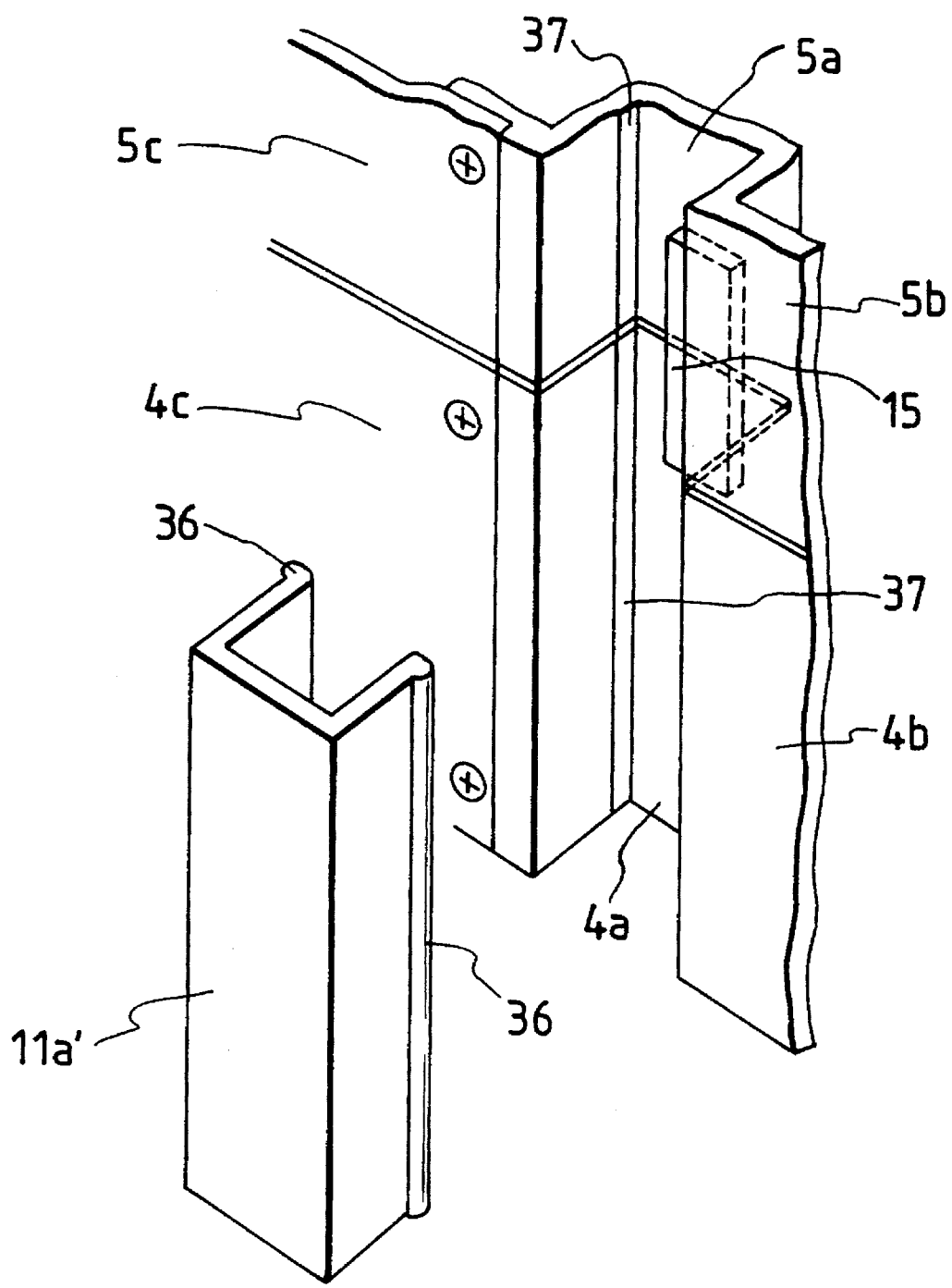
FIG. 7 is an explanatory view showing the piping passages of the liquid chromatograph of FIG. 1.

FIG. 2 is an enlarged explanatory view showing a pump unit constituting the liquid chromatograph of FIG. 1; FIG. 3 is a front elevation showing the pump unit constituting the liquid chromatograph of FIG. 1; FIG. 4 is a partially sectional righthand side elevation showing the pump unit constituting the liquid chromatograph of FIG. 1; FIG. 5 is a section of the casing and the pump unit as taken along line A—A of FIG. 3; FIG. 6 is a section of the casing and the pump unit as taken along line B—B of FIG. 3; and FIG. 7 is an explanatory view showing the piping passages of the liquid chromatograph of FIG. 1.

As described above, the aforementioned casing 4 acts as the pump unit in the present embodiment. In FIG. 2, this casing 4 is equipped with a front cover 4b constituting the front portion thereof and two side covers 4c constituting the two side portions thereof.

In the present embodiment, the front cover 4b is molded of a resin, and the side covers 4c are made of a metal plate, but may also be molded of a resin.

The front face of the front cover 4b has its front portion formed into a bulging curved face 18 to provide a smoothened uniform surface on the outer face of the front cover from the front face to the side faces.

The front cover 4b is formed at its two side end portions with band-shaped vertical face portions 20a which are separated from the inner face by dividing vertical grooves 19a.

The inner face of the dividing vertical grooves 19a is provided with a band-shaped horizontal transparent plate 21 at its upper portion, a hinged door 22 at its lower righthand side, and a control panel 23 and a front plate 24 at its lower lefthand side.

The bulging curved face 18 is formed of the face portions 20a, the transparent plate 21, the hinged door 22 and the front plate 24, and only the control panel 23 is recessed from the curved face 18.

The hinged door 22 is provided to cover a pipe connecting chamber 25 (as shown in FIG. 3) disposed inside thereof and is molded integrally with the face portion 20a at the righthand side, as viewed from the front. The door 25 is hinged to the front cover 4 in an openable/closable manner by means of hinges 26 mounted on the upper and lower end portions of the righthand face portion 20a.

In the present embodiment, the hinged door 22 and the righthand face portion 20a are integrally molded, but may be molded separately from each other.

The transparent plate 21 is provided to cover a display 27 arranged inside thereof and is equipped with a power switch 28 at the lefthand side.

The control panel 23 is formed of a sheet 23a having a variety of keys printed thereon and is equipped therein with a (not-shown) control board 29.

In the present embodiment, the control panel 23 is formed of the sheet 23a, as described above, but may be composed of control switches or dial switches made of a plurality of ordinary keys.

In this modification, it is desirable that the leading ends of the control switches or dial switches may not protrude from the surface of the curved face 18.

The front cover 4b is formed in its two side faces with the vertically bored-through, recessed first passage 4a, which are covered with covers 11a.

These covers 11a are so hinged (although not shown) to the front cover 4b that they can be opened/closed and that they are flush with the surface of the front cover 4b, when closed, to provide a smoothened uniform surface.

The two ridges, at which the side covers 4c and the top face of the casing 4 intersect, are individually formed with the notches 17.

These notches 17 are positioned near the center of gravity, as taken in the depthwise direction of the casing 4.

On the other hand, the casing 4 is formed in its top face with a plurality of (e.g., four, as shown) recessed leg receiving portions 30 and is equipped on its bottom face with legs 31 which are positioned to correspond to the leg receiving portions 30.

These legs 31 and their receiving portions 30 are also arranged in the corresponding positions on the remaining casings 5, 6 and 7. The leg receiving portions 31 are substantially sized to receive the legs 31 of another casing.

On the upper face of one casing 4 thus constructed, there is stacked another casing 5 such that the legs 31 of the casing 5 are fitted in the leg receiving portions 30 of the casing 4. Thus, the casings can be sequentially stacked stably with a reduced gap inbetween. In this stacked state, moreover, the first passages 4a to 8a are formed to communicate with each other.

In the embodiment thus far described, the casing 4 is supported by the four legs 31, but the supporting structure should not be limited thereto. For example, each casing may be equipped on its bottom face with protruding legs and formed in its top face with recessed leg receiving portions which are positioned and sized to receive the legs. With this structure, too, the legs may be fitted in their receiving portions to stack the casings stably with a small gap.

The internal structure of the pump unit of the casing 4 will be described in the following with reference to FIGS. 3 to 6. As shown in FIG. 3, the pipe connecting chamber 25 is recessed from the curved face 18 so that it accommodates a pump head 32, a drain valve 33 and a plurality of branching valves 34.

The pipe connecting chamber 25 is formed with a second passage 46 (as shown in FIG. 5) and a third passage 47, which are to be connected to the lefthand and righthand first passages 4a.

The second passage 46 is provided for connecting the pipe connecting chamber 25 and the first passage 4a, which is adjacent to the former and located at the righthand side, as viewed from the front, and is formed of an opening extending through the side wall of the first passage 4a.

The third passage 47 is provided for connecting the pipe connecting chamber 25 and the first passage 4a at the lefthand side, as viewed from the front, and is formed in the front plate 24.

The casing 4 is equipped in its back face with a terminal connecting portion 35 (as shown in FIG. 4). In this terminal connecting portion 35, arranged the terminals are centrally arranged to provide the connection with the power supply and the signal connections with other devices.

Since, in the present embodiment, the less frequently used connecting portions with the power supply cord and the signal lines are concentrated in the terminal connecting portions 35 disposed in the back face, the connections between the casing 4 and the other individual casings 5, 6, 7 and 8 are carried out at the inconspicuous back face whereas the frequently used connections with the pipe 16 are carried out through the first passages 4a which are formed at the two sides of the casing 4. It is quite natural that a passage having a construction similar to that of the first passage 4a may be provided for connecting the power supply cord and the signal lines.

In the foregoing structure (as shown in FIG. 1), the cover 11a can be opened from or closed on the front cover 4b by means of the hinges 26. In FIGS. 2, 5, 6 and 7, however, there is provided a removable cap type structure 11a' which has operations and effects similar to those of the hinge structure.

Here will be described the first passage 4a which is equipped with the cap-type cover 11a'.

As shown in FIGS. 5 and 6, the first passage 4a, which is formed close to the control panel 23 and located at the lefthand side, as viewed from the front, is disposed at the back of the control board 29 of the control panel 23 so that the first passage 4a and the control board 29 overlap, as viewed from the front.

Thanks to this structure, the control panel 23 can minimize the width of the casing 4 while retaining the front area necessary for its functions.

As shown in FIG. 7, moreover, the cover 11a' is formed to have such a generally C-shaped section as is formed with ridges 36 on the outer sides of the two leading end portions of its opening. In the corners of the first passage 4a, there are formed grooves 37 which engage with the ridges 36 when the cover 11a' is fitted in the first passage 4a.

The fitting 15 is formed into a rectangular shape for providing the communication between the first passage 4a and the first passage of another casing and is fixed by means of screws, as shown in FIG. 7, so as to provide the communication and engagement between the first passage 4a and the first passage 5a formed in the casing 5.

Next, the external structure of the liquid chromatograph body of FIG. 1 and the structures of the remaining casings will be described below with reference to FIGS. 8 to 11.

Figure 8:
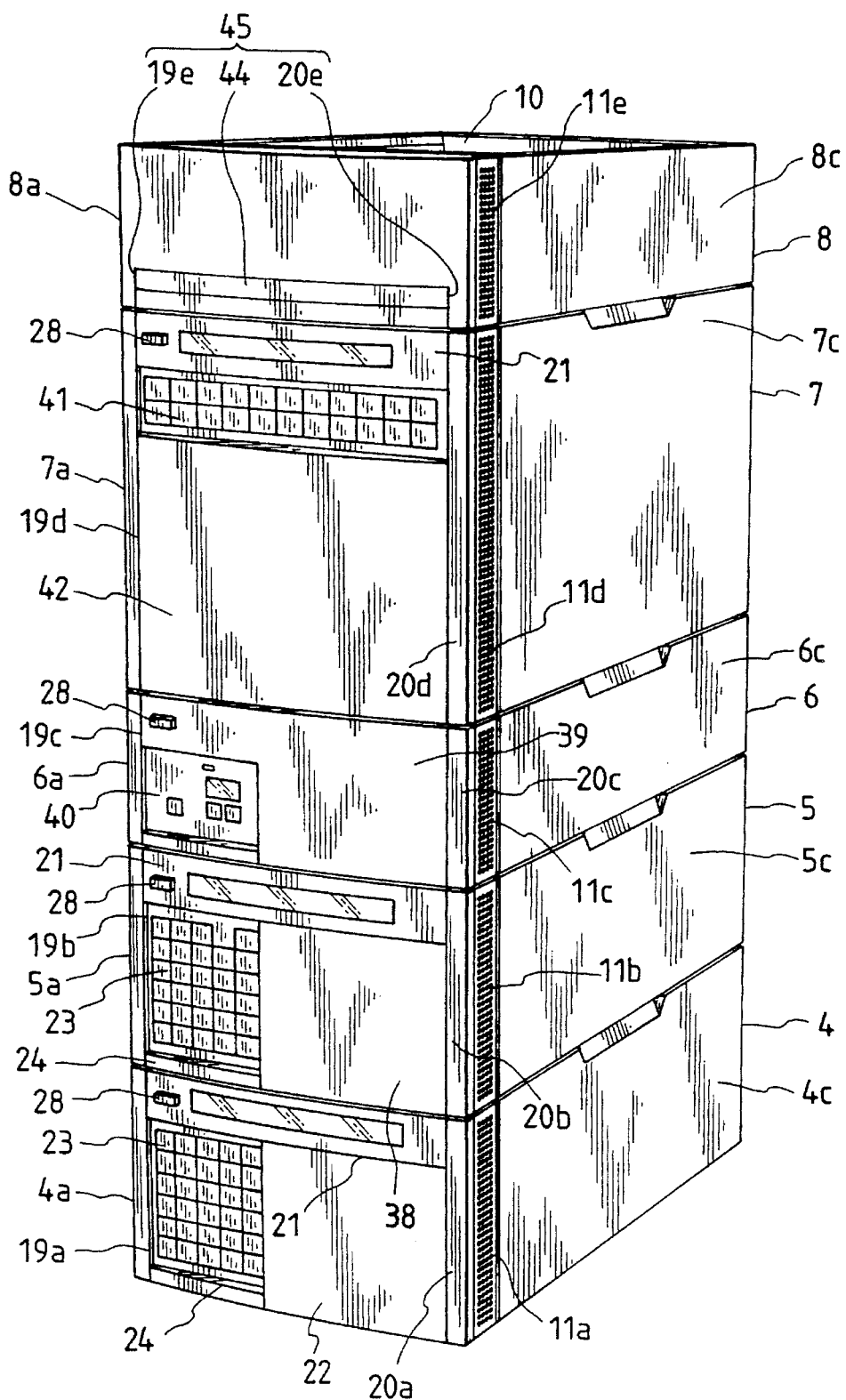
FIG. 8 is a perspective view showing the exterior of the liquid chromatograph body of FIG. 1.
Figure 9:
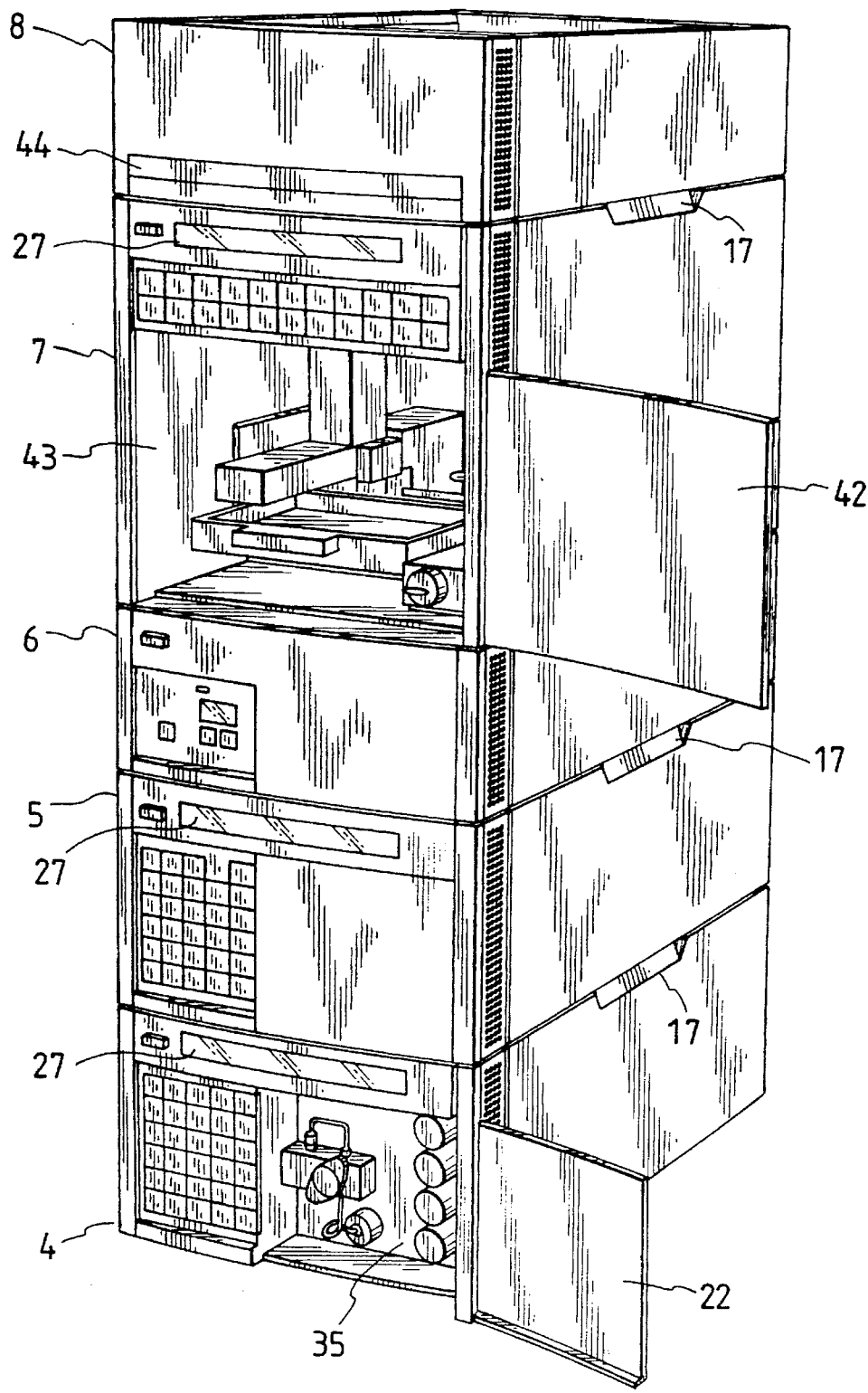
FIG. 9 is a perspective view showing the liquid chromatograph body of FIG. 1 with an open door.
Figure 11:
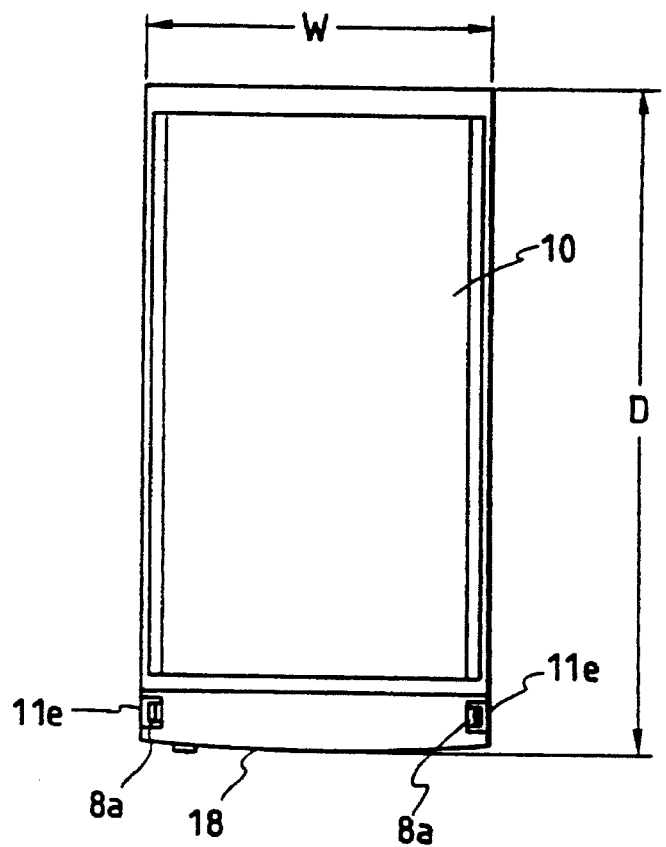
FIG. 11 is a dimensioned top plan view showing the liquid chromatograph body of FIG. 1.

FIG. 8 is a perspective view showing the exterior of the liquid chromatograph body of FIG. 1; FIG. 9 is a perspective view showing the liquid chromatograph body of FIG. 1 with an open door; FIG. 10 is a dimensioned diagram showing the liquid chromatograph body of FIG. 1, of which (A) is a dimensioned diagram showing the front view of the liquid chromatograph body of FIG. 1 and (B) is a dimensioned diagram showing the righthand side of the liquid chromatograph body of FIG. 1; and FIG. 11 is a dimensioned top plan view showing the liquid chromatograph body of FIG. 1.

As shown in FIGS. 8 and 9, the external structures of the casings 5, 6 and 7 are made similar to that of the casing 4 but different in the constructions of the front cover in accordance with the functions.

The casing 5 acting as the detector unit has its front cover 5b formed of: face portions 20b at the two side ends of the front face, as divided by dividing vertical grooves 19b; a transparent plate 21 at the central upper portion; a front plate 38 at the righthand lower portion of the center; a control panel 23 at the lefthand lower portion of the center; and a front plate 24. Thus, the front cover 5b of the casing 5 has an entire layout identical to that of the casing 4.

The casing 6 acting as the column oven unit has its front cover 6b formed of: face portions 20c at the two side ends of the front face, as divided by dividing vertical grooves 19c; a front plate 39 at the central portion; and a control panel 40.

The casing 7 acting as the sample feed unit has its front cover 7b formed of: face portions 20d at the two side ends of the front face, as divided by dividing vertical grooves 19d; a transparent plate 21 at the central upper portion; a transparent plate 21 at the central intermediate portion; a control panel 41 having the same size as that of the transparent plate 21; and a hinged door 42 at the central lower portion.

Since the casing 7 acts as the sample feed unit, it is equipped with: a device accommodating chamber 43 formed therein and equipped with a table holding thereon a plurality of (not-shown) sample bottles, (not-shown) reaction bottles and (not-shown) reagent bottles, and a moving part for the dispensing, diluting and adding operations; and a large hinged door 42 for covering the device accommodating chamber 43.

The cover 8 acts as a reservoir unit having no internal device and is stacked at the uppermost position so that it is partially different from the remaining casings 4 to 7.

Specifically, the casing is formed on the lower portion of the front face of its front cover 8a with a divided portion 45 which is divided by a lefthand dividing vertical groove 19e, a horizontally elongated aperture 44 and a righthand dividing vertical groove 19e.

The divided portion 45 thus formed has its lefthand side continued to the dividing vertical grooves 19a to 19d, which are formed in the lefthand sides of the casings stacked below the casing 8, and its righthand side continued to the dividing vertical grooves 20a to 20d, which are formed in the righthand sides of the casings stacked below the casing 8, thus forming an inverted u-shape.

As described above, the front faces of the front covers 4b to 8b of the covers 4 to 8 are so formed that their components other than the individual control panels 23 of the casings 4 and 5, the control panel 40 of the casing 6 and the control panel 41 of the casing 7 provide the smoothened, bulging curved face 18, as viewed from the front face.

Moreover, the individual front covers 5b to 8b are formed with the first passages 5a to 8a, which are made similar to and disposed in the same positions as those of the first passage 4a formed in the casing 4, and are equipped with covers 11b to 11e.

As a result, the liquid chromatograph body 2 is formed with the first passages 4a to 8a which are provided with the vertical communication when the casings 4 to 8 are laminated one on another.

Moreover, the casings 5 to 8 may be formed with second or third passages similar to that of the casing 4 so that the casings 4 to 8 can be piped with each other without having pipe 16 exposed to the outside by connecting the insides or the device accommodating chambers 43 of the individual casings with the first passages 5a to 8a.

According to the present embodiment, as described above, the individual casings 4 to 8 can have their front faces vertically continued by forming the two side ends of the front faces of the casings with the face portions 20a to 20d through the dividing vertical grooves 19a to 19d.

Moreover, the units individually equipped with the displays 27 are further equipped with the transparent plates 21 in the same positions and with the same sizes.

Still moreover, the individual casings have their front covers 4b to 8b formed with the front face shapes having the bulging curved faces 18, as viewed from the top face, to enhance the rigidities of the individual components forming the front faces. Thanks to the aforementioned arrangement, the liquid chromatograph body 2 can provide an integrated single appearance while enhancing the cleanability.

On the other hand, the casings 5, 6 and 7 are provided like the casing 4 with the notches 17 in their side covers 5c, 6c, and 7c and the leg receiving portions 30 and the legs 31 on their top and bottom faces, and the remaining casing 8 is equipped with the legs 31 on its bottom face.

As a result, the leg receiving portions 30 and the legs 31 of the upper and lower casings can be fitted so that their gaps can be reduced to reduce their total height thereby providing the stacked liquid chromatograph body 2 stably with a lower center of gravity. In this stacked state, the liquid chromatograph body 2 is formed with the first passages 4a to 8a communicating with each other.

With this construction, the individual casings can be mounted by means of the fittings 15 (as shown in FIG. 7) and separated by using the notches 17 as hooks.

On the other hand, the casings 5, 6 and 7 are equipped like the casing 4 on their back faces with the terminal connecting portions 35 so that the power supply and the signals are connected at the back faces of the individual casings.

The specific sizes of the casings 4 to 8 in the present embodiment are exemplified in FIGS. 10(A) and 10(B) and FIG. 11.

All of the casings have their width W and depth D commonly set to 260 mm and to 500 mm, respectively, to equalize the sizes of their top faces. The casing 4 is given a height 4H of 150 mm; the casing 5 a height 5H of 150 mm; the casing 6 a height 6H of 105 mm; the casing 7 a height 7H of 235 mm; and the casing 8 a height 8H of 105 mm. As a result, the total height H of the casings 4 to 8 is 765 mm.

With reference to FIG. 12, here will be described the passages for feeding the samples and the reagents from the eluent bottles 9a and the cleaning fluid bottles 9b of the liquid chromatograph body 2 to the individual casings through the pipe 16.

FIG. 12 is an explanatory diagram showing the piping of the liquid chromatograph body of FIG. 1.

In FIG. 12 showing the pipe 16 for the samples and the reagents: (A) presents a lefthand side view; (B) a front face view; and (C) a righthand side view.

As shown in FIG. 12, the casing 8 acting as the reservoir unit having the reagent accommodating portion 10 is stacked in the highest position. The pipe 16 connected to the eluent bottle 9a in the reagent accommodating portion 10 is so piped through the first passages 8a to 5a at lefthand side, as viewed from the front face, to the first passage 4a as to lead to the pipe connecting chamber 25 through the (not-shown) third passage 47 until it is connected to the pump head 32.

The eluent pressurized by the pump head 32 flows from the pump head 32 through the branching valve 34 and further through the (not-shown) second passage 46 to the first passage 4a and is fed through the first passages 5a, 6a and 7a and the (not-shown) second passage of the casing 7 acting as the fuel feed unit to a piping connector 48 disposed in the casing 7.

The liquid thus dispensed, diluted and added in the casing 7 acting as the fuel feed unit 7 is guided from the piping connector 48 again through the second passage of the casing 7, the first passages 7a and 6a and the (not-shown) second passage of the column oven unit of the casing 6 in the recited sequence to a piping connector 49 which is disposed in the column oven unit of the casing 6.

The ingredient liquids thus separated by the column in the column oven unit are guided from the piping connector 49 again through the second passage and further from the first passages 6a and 5a through the (not-shown) second passage of the casing 5 acting as the detector unit to a piping connector 50.

The liquids having their ingredients analyzed by the detector unit of the casing 5 are guided from the piping connector 50 through the second passage of the casing 5 and through the first passages 5a, 6a, 7a and 8a until they are disposed into a disposal bottle 9c disposed in the reagent accommodating portion 10 of the reservoir unit of the casing 8.

The cleaning fluid in its bottle 9b is pumped like the eluent from the pump head 32 through the drain valve 33, the third passage 47 and the first passages 4a to 7a along the dotted line indicated by arrow A2, until it is disposed to the disposal bottle 9c.

Along the dotted line indicated by arrow A3, moreover, the cleaning fluid is also pumped from the piping connector 48 through the (not-shown) third passage of the casing 7 and the first passages 7a and 8a until it is disposed to the disposal bottle 9c.

In the present embodiment, the first passages 4a to 8a are given such an effective area as can accommodate four pipes.

In the present embodiment, the various pipes 16 are evenly arranged in the first passages 4a to 8a arranged at the two sides of the individual units. For example, however, the first passages 4a to 8a at the lefthand side may be used for piping the eluent feeding pipe 16 to the pump unit whereas the first passages 4a to 8a at the righthand side may be used for piping the feed pipe 16 from the pump unit of the casing 4 to the remaining casings 5, 6, 7 and 8.

Moreover, the handling at the pipe connecting time can be improved by forming passages for all kinds of pipes by providing other passages for the cleaning and disposing pipes 16.

In this modification, the piping distance can be shortened by arranging the piping connectors of the individual units close to the corresponding passages.

Figure 13:
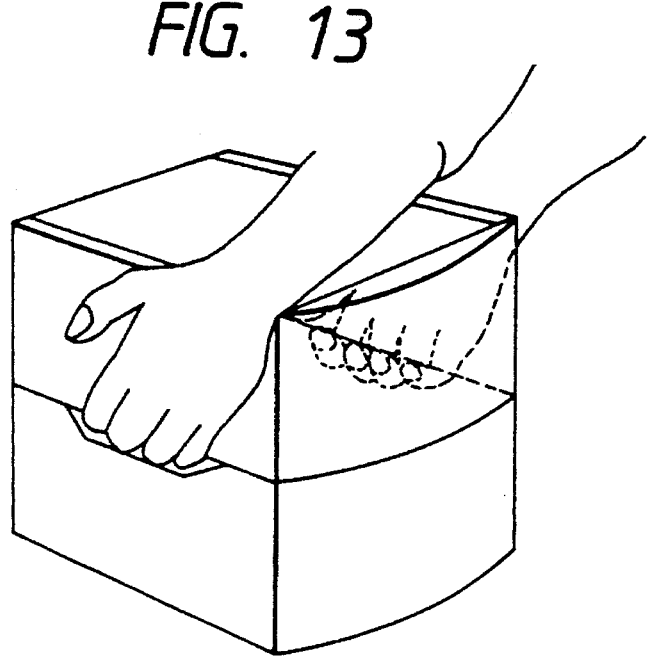
FIG. 13 is an explanatory view illustrating the casing stacking operation of the liquid chromatograph body of FIG. 1.

Here will be described the installation and operation of the liquid chromatograph according to the present embodiment. FIG. 13 is an explanatory view illustrating the casing stacking operation of the liquid chromatograph body of FIG. 1.

In the present embodiment, each of the casings constructing the liquid chromatograph body 2 can be selected for a sample to be analyzed and is stacked on another casing.

In the stacking operation, each casing has its legs 31 fitted in the leg receiving portions 30 of the underlying casing so that the gap inbetween can be eliminated while preventing their horizontal displacement.

In these stacking and separating operations, each casing can be supported at its notches 17 so that the operator is protected and safe because a finger will not be clamped during the operations, as shown in FIG. 13.

Moreover, the individual casings are connected to each other through the first passages 4a to 8a by the fittings 15. These connections through the fittings 15 can be small-sized because a higher strength than that of the prior art is not required thanks to the fitting engagements between the legs 31 and their receiving portions 30.

Moreover, the connections of the pipes 16 between the individual casings are effected through the vertically communicating first passages 4a to 8a and through the second passage 46 and third passage 47 connecting the first passages 4a to 8a and the pipe connecting portions in the casings.

Moreover, the fittings 15 and the pipes 16 can be shielded from the outside by covering the first passages 4a to 8a with the covers 11a to 11e.

On the other hand, the power supply and the signal wiring lines are connected at the terminal connecting portions 35 disposed at the back face of each casing.

In the liquid chromatograph 1, the individual casings (except the casing 8) constructing the liquid chromatograph body 2 and the data processor 2 are equipped with the independent power switches 28.

The individual casings 4 to 7 can have their individual operating conditions set through the control panels 23, 40 and 41 thereof by turning ON the individual power switches 28.

Incidentally, when the power switch 28 of the main casing such as the pump unit of the casing 4 or the data processor 3 is turned ON, the liquid chromatograph 1 is turned ON in its entirety to start the analysis.

As described above, according to the present embodiment, the individual casings 4 to 8 are equipped with the first passages 4a to 8a, which establish the communication when in the stacked state, and the second passage 46 (and the third passage 47). As a result, the pipe 16 can be connected through the first passages 4a to 8a and the second passage 46 so that the piping operation can be facilitated.

Thus, the pipe 16, which has been loosely piped in the prior art to meander through the gaps between the individual casings, can be connected straight through the aforementioned two passages.

As a result, the pipe 16 can be connected at the shortest distance to reduce the amount of liquid to flow in the pipe 16. Thus, the total amounts of reagents and cleaning fluid to be fed can be reduced to shorten the setup and cleaning time periods and to improve the accuracy of microanalysis of the mixture sample.

Moreover, the pipe 16 is arranged in the first passages 4a to 8a and the second passage 46 so that it is not erroneously broken. As a result, the safety can be improved while preventing the precious analysis data from being lost or the dangerous reagent being fed in the pipe 16 from being scattered.

In addition, the pipes 16 are concentrated along the first passages 4a to 8a so that the handling for installing and removing the pipes can be improved.

On the other hand, the casings 4 to 8 are formed with: the front covers 4b to 8b forming the front faces of the casings and having the smoothened uniform surfaces; and the dividing vertical lines 19a to 19e which are so located at the two side ends of the front faces as to vertically continue in the stacked state and to form the face portions 20a to 20e at the sides ends. As a result, the liquid chromatograph is given a vertically continuous, integral appearance to match the indoor environment.

Moreover, the individual casings 4 to 8 are equipped with: the protruding legs 31 on their bottom faces; the leg receiving portions 30, which are formed in the upper faces of the casings in the positions corresponding to the legs 31 for receiving the legs 31 substantially; and notches 17 in the two side ends of the top and bottom faces thereof. As a result, the total system can be stably constructed to provide an integral structure having a reduced total height while retaining the each stacking and separating advantages.

Furthermore, the fittings 15 for fixing the individual casings 4 to 8 to each other can have their strength reduced by fitting the legs 31 in the leg receiving portions 30, so that they can be small sized. Moreover, the first passage 4a to 8a can be shielded by the covers 11a to 11e to improve the appearance and the safety.

Here will be described the casings which are applied to the liquid chromatograph according to a second embodiment of the present invention.

Figure 14:
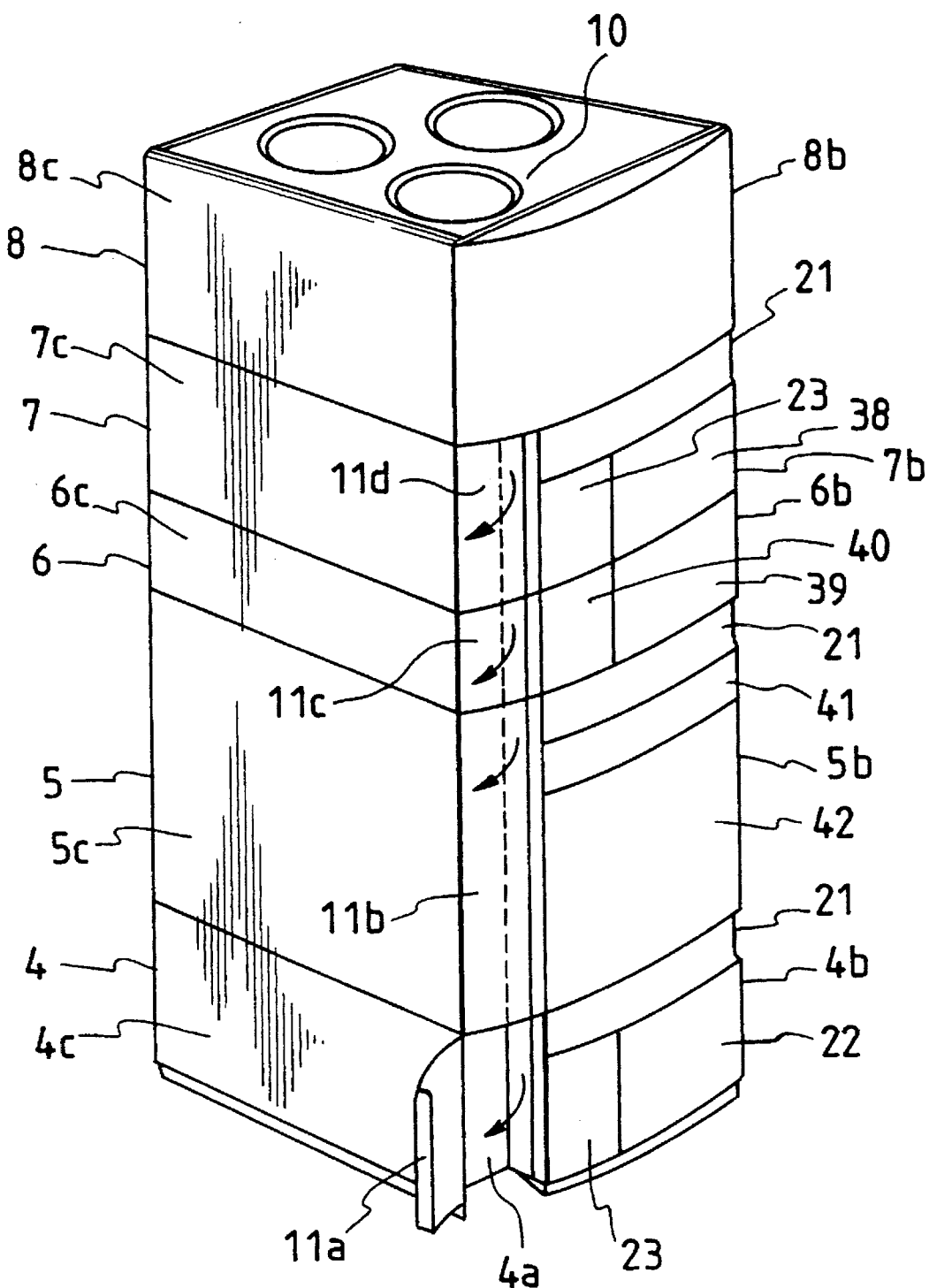
FIG. 14 is a perspective view showing the exterior of a liquid chromatograph body according to another embodiment of the separating analyzer of the present invention.

FIG. 14 is a perspective view showing the exterior of a liquid chromatograph body according to the second embodiment of the separating analyzer of the present invention. The same reference numerals appearing in FIG. 14 as those appearing in FIGS. 1 to 13 designate the equivalent members and portions so that their repeated description will be omitted.

In FIG. 14, the first passages 4a to 8a are formed in only one side end of the front face of each casing as is the care for the first embodiment.

As shown in FIG. 14, the liquid chromatograph body 2 is constructed of the box-shaped casings 4 to 8 which are given the identical top face shape so that they can be stacked.

These casings 4 to 8 excluding the uppermost casing 8 are interchangeably stacked according to varying the mixture sample to be separated and analyzed.

In the present embodiment: the casing 4 is assigned to the pump unit; the casing 5 to the sample feed unit; the casing 6 to the column oven unit; the casing 7 to the detector unit; and the casing 8 to the reservoir unit. These casings 4 to 8 are composed of front covers 4b to 8b forming the front portions and side covers 4c to 8c forming the back portions.

The front covers 4b to 7b are formed in the lefthand sides of their front faces with the dividing vertical grooves 19a to 19d and at their lefthand end portions with the covers 11a to 11d having the face portions 20a to 20d.

The covers 11a to 11d can be opened/closed, as indicated by arrows, by (not-shown) hinges disposed at the lefthand end portions.

The covers 11a to 11d are formed therein with the first passages 4a to 7a for providing the communications between the casings 4 to 7 in the stacked state.

The remaining casing 8 is formed in its bottom with the first passage 8a which is positioned to correspond to the first passage 7a when it is stacked on the casing 7.

Thanks to this structure of the first passages 4a to 8a, the individual casings 4 to 8 can be piped without exposing the pipes 16 to the outer surfaces.

Moreover, reference numeral 10 designates a reagent accommodating portion 10 equipped on its top face with a plurality of accommodating portions for circular bottles; numeral 21 indicates a transparent plate; numerals 23, 40 and 41 indicate control panels; numerals 22 and 42 indicate hinged doors; and numeral 39 indicates a front plate.

Because the casings 4 to 8 are equipped with the legs 31 on their bottom faces whereas the casings 4 to 7 are formed with leg receiving portions 30 in their top faces, they can be stacked with a small gap.

Figure 15:
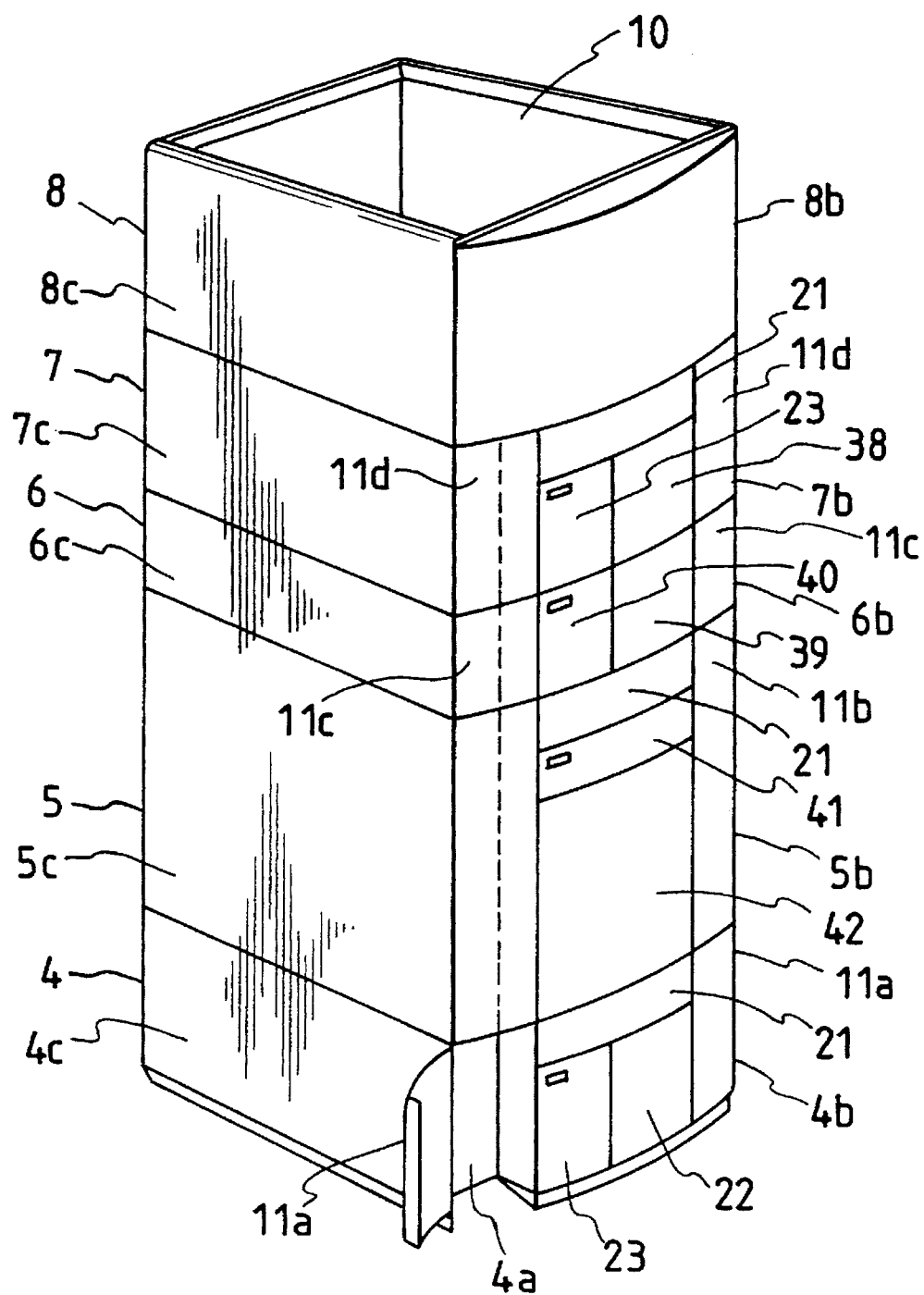
FIG. 15 is a perspective view showing the exterior of a liquid chromatograph body according to still another embodiment of the separating analyzer of the present invention.

Here will be described the casings accommodating the liquid chromatograph according to the third embodiment of the present invention. FIG. 15 is a perspective view showing the exterior of a liquid chromatograph body according to the third embodiment of the separating analyzer of the present invention. The same reference numerals as those appearing in FIGS. 1 to 14 designate the equivalent members and portions so that their repeated description will be omitted.

As shown in FIG. 15, the present embodiment is formed with the first passages 4a to 7a at the two side ends of the front faces.

The liquid chromatograph body 2 is constructed of the box-shaped casings 4 to 8 which are given the identical top face shape so that they can be stacked one on another.

The casings 4 to 8 are given the same structures as those of the second embodiments, shown in FIG. 14.

The casings 4 to 8 are composed of the front covers 4b to 8b forming the front portions and the side covers 4c to 8c forming the back portions. The casings 4 to 8 are formed with the dividing vertical grooves 19a to 19d in the two sides of the front faces of the front covers 4b to 7b and the covers 11a to 11d having the face portions 20a to 20d at the two side ends.

These covers 11a to 11d can be opened/closed by the (not-shown) hinges disposed at the two side ends.

The covers 11a to 11d are formed therein with the first passages 4a to 7a for providing the communications between the casings 4 to 7 in the stacked state.

The casing 8 is formed in its bottom face with the first passage 8a which is positioned to correspond to the first passage 7a when it is stacked on the casing 7.

Thanks to the structure from the first passages 4a to 8a, the individual casings 4 to 8 can be piped without exposing the pipes 16 to the outer surface.

According to the embodiment described above, the first passages 4a to 8a are arranged in the front face so that the piping operation can be facilitated.

Moreover, the first passages 4a to 8a can have their surfaces covered with the covers 11a to 11d having the face portions 20a to 20d so that they can be shielded. At the same time, the face portions 20a to 20d thus formed are vertically continuous so that the liquid chromatograph body 2 can be given an integral appearance.

Figure 16:
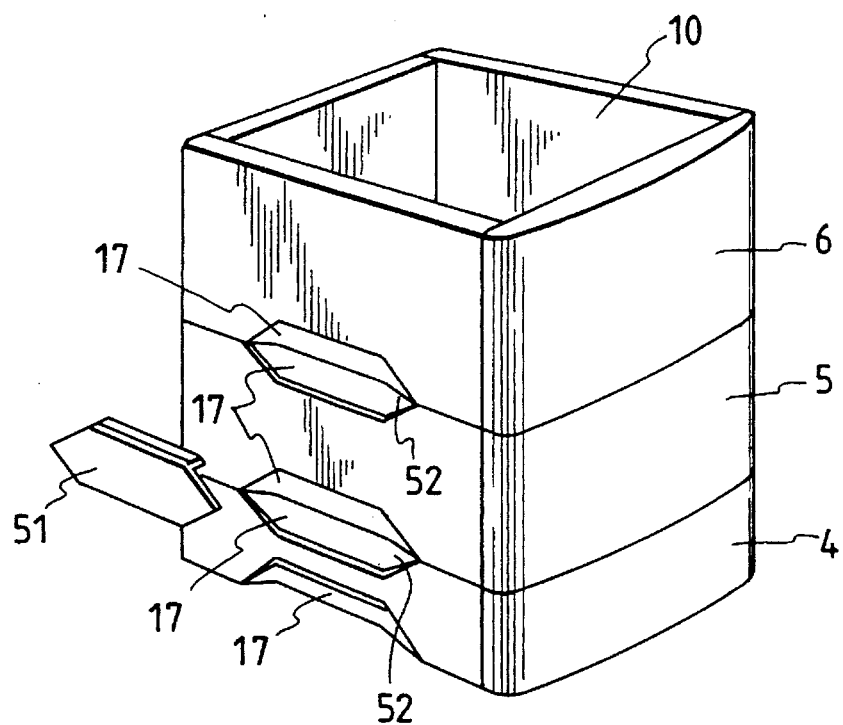
FIG. 16 is a perspective view showing the exterior of a liquid chromatograph body having a stacked casing, according to still another embodiment of the separating analyzer of the present invention.
Figure 17:
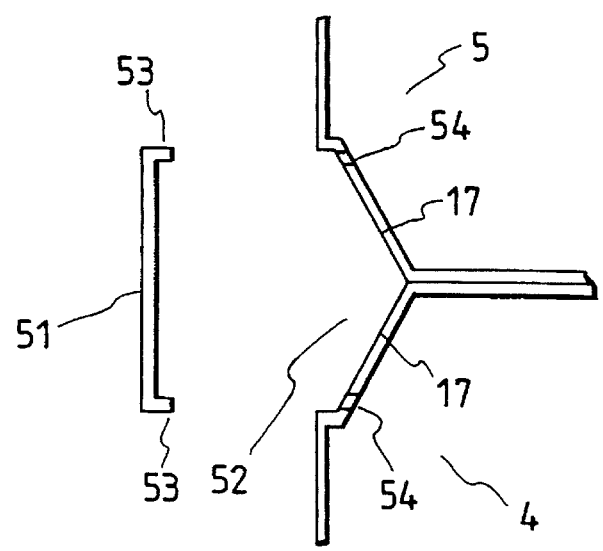
FIG. 17 is an explanatory view showing a portion of the casing of FIG. 16.

Here will be described the casing for accommodating the liquid chromatograph according the fourth embodiment of the present invention. FIG. 16 is a perspective view showing the exterior of a liquid chromatograph body having a stacked casing, according to the fourth embodiment of the separating analyzer of the present invention. FIG. 17 is an explanatory view showing a portion of the casing of FIG. 16. The same reference numerals as those appearing in FIGS. 1 to 15 designate the equivalent members and portions so that their repeated description will be omitted.

As shown in FIG. 16, according to the present embodiment, each of the casings is formed with the notches at its two side ends. There are provided fixing plates 51 for plugging the notches 17 when the casings are stacked, to fix the stacked casings and for exposing the notches 17 to the outside, when the casings are separated, to release the stacked casings from their fixed states.

In FIG. 16, the casings 4 and 5 are equipped with the (not-shown) legs 31 and the (not-shown) leg receiving portions 30 whereas the casing 6 is equipped with the (not-shown) legs 31 so that the casings 4, 5 and 6 are stacked one on another without any gap.

The casing 6 is stacked in the uppermost position and is equipped with the reagent accommodating portion 10. The casing 6 is formed with the notches 17 at the two sides of its bottom face.

The casings 4 and 5 are also formed with the notches at the two sides of their upper and lower faces.

Here, the notches 17 thus formed in the casings 4, 5 and 6 are positioned to vertically align with each other when they are stacked.

The fixing plate 51 is sized to correspond to a recess 52 defined by the upper and lower notches 17, when the casings 4, 5 and 6 are stacked. The fixing plate 51 is formed with pawls 53 at its upper and lower portions whereas the notch 17 is formed with retaining holes 54.

The fixing plate 51 has its pawls 53 retained by the retaining holes 54 when it is fitted in the recess 52. Thanks to this structure, the upper and lower casings have their two side notches 17 covered with the fixing plates 51, while being fixed, to provide flat side faces.

Figure 18:
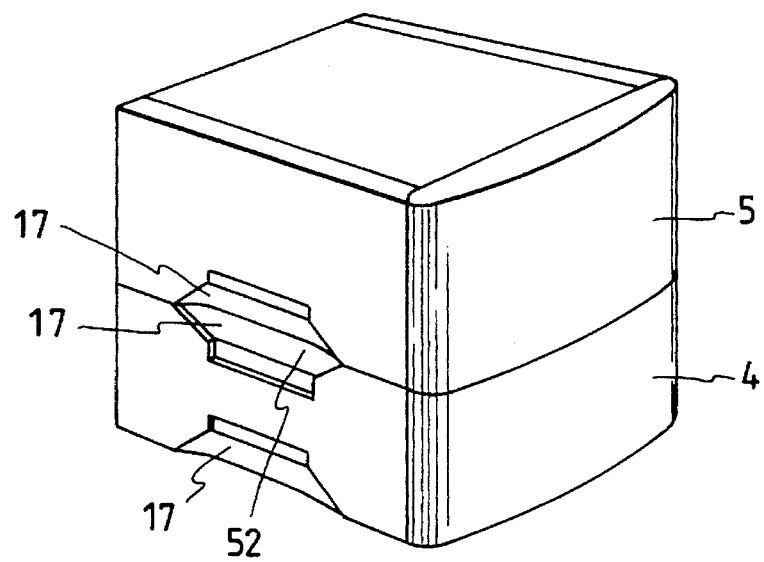
FIG. 18 is a perspective view showing the exterior of a liquid chromatograph body having a stacked casing, according to still another embodiment of the separating analyzer of the present invention.
Figure 19:
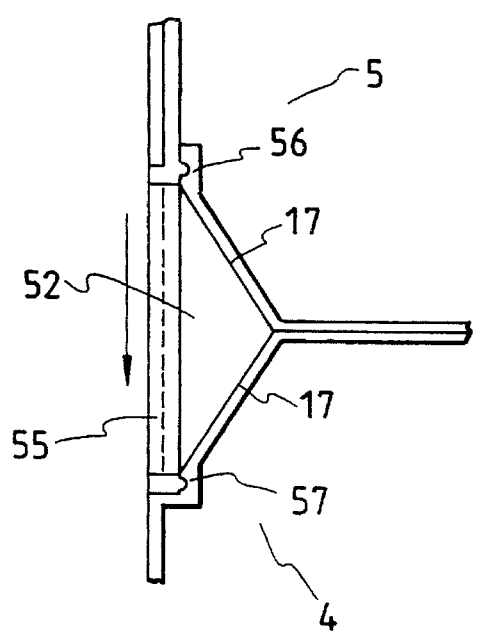
FIG. 19 is an explanatory view showing a portion of the casing of FIG. 18.

FIG. 18 is a perspective view showing the exterior of a liquid chromatograph body having a stacked casing, according to the fifth embodiment of the separating analyzer of the present invention. FIG. 19 is an explanatory view showing a portion of the casing of FIG. 18.

The same reference numerals as those appearing in FIGS. 1 to 17 designate the equivalent members and portions so that their repeated description will be omitted.

FIG. 18 shows the fifth embodiment having effects similar to those of the third embodiment of FIG. 16.

As shown, the casings 4 and 5 are stacked with a reduced gap inbetween and with the recess 52 being formed in their side faces by the two notches 17. There is provided a fixing plate 55 which is slidably mounted in the notch 17 of the casing 5 stacked in the upper position.

The fixing plate 55 is sized to cover the recess 52 and is equipped with pawls 56 at its leading ends. The casing 4 in the lower position is formed with a retaining hole 57 in its notch 17. The pawl 56 is retained in the retaining hole 57 such that the fixing plate 55 is extracted to cover the recess 52 when the casings 4 and 5 are in the stacked state.

Thanks to this structure, the upper and lower casings 4 and 5 have their two side notches 17 covered, while being fixed, to provide flat side faces.

Figure 20:
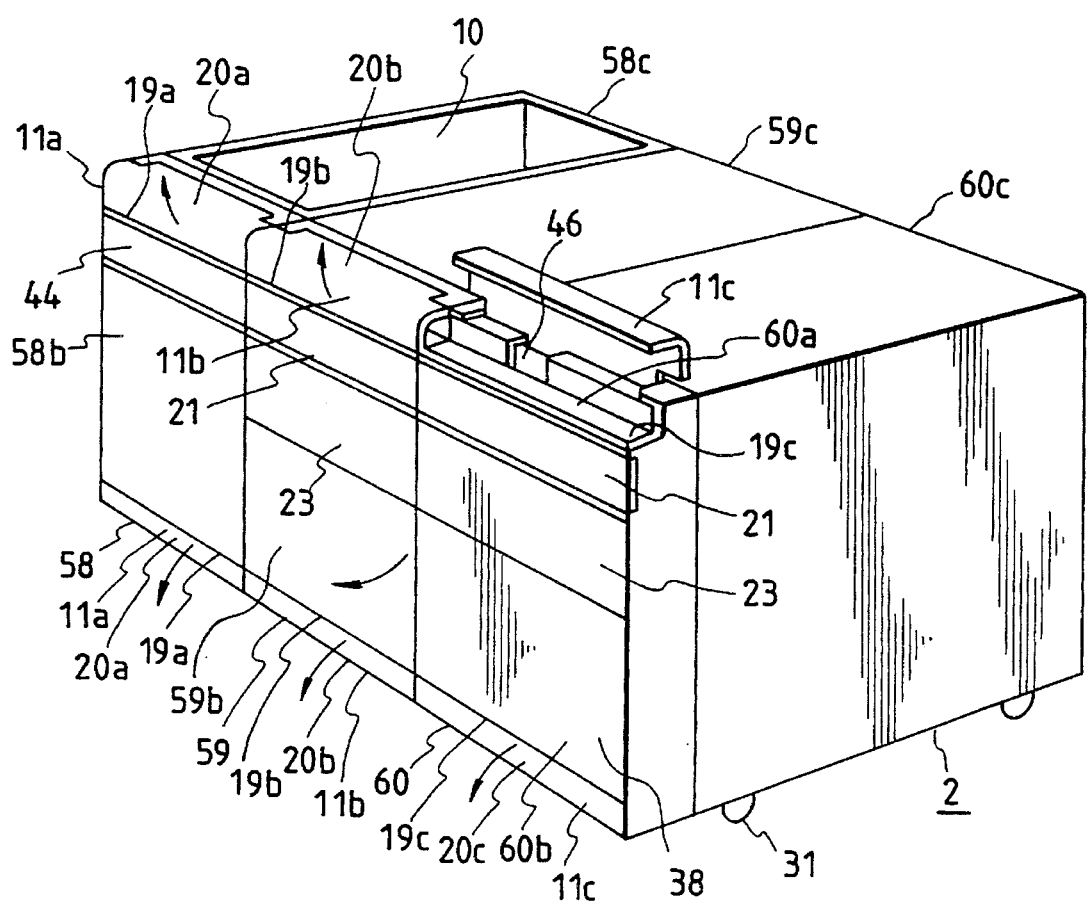
FIG. 20 is a perspective view showing the exterior of a liquid chromatograph body according to still another embodiment of the separating analyzer of the present invention.

Here will be described a liquid chromatograph according to the sixth embodiment of the separating analyzer according to the present invention. FIG. 20 is a perspective view showing the exterior of a liquid chromatograph body according to the sixth embodiment of the separating analyzer of the present invention.

Incidentally, the same reference numerals as those appearing in FIGS. 1 to 19 designate the equivalent members and portions so that their repeated description will be omitted. The description will be made upon only the new reference numerals.

Reference numerals 58, 59 and 60 designate box-shaped casings; numerals 58b, 59b and 60b designate the front covers; and numerals 58c, 59c and 60c designate the back covers.

According to the present embodiment, as shown in FIG. 20, the individual casings are horizontally juxtaposed in series and equipped with first passages 58a to 60a on their outer surfaces.

As shown, the liquid chromatograph body 2 is constructed of the box-shaped casings 58 to 60 which are formed to have an identical side face shape so that they can be horizontally juxtaposed in series. These casings 58 to 60 are interchangeably juxtaposed according to the mixture sample to be separated and analyzed.

The present embodiment presents the minimum system which has its casing 58 assigned to the reservoir unit, its casing 59 to the pump unit and its casing 60 to the detector unit. These casings 58 to 60 are constructed of the front covers 58b to 60b forming the front portions and the back covers 58c to 60c forming the back portions.

The front covers 58b to 60b are provided in the upper and lower portions of the front faces with dividing horizontal grooves 19a to 19c and at the upper and lower ends with covers 11a to 11c having face portions 20a to 20c.

The covers 11a to 11c are given L-shaped sections so that they can be vertically opened/closed, as indicated by arrows, by the (not-shown) hinges disposed at their end portions.

The covers 11a to 11c are formed therein with first passages 58a to 60a for providing the communication between the casings 58 to 60 in the juxtaposed state.

The passage 46 is the second one for connecting the first passages 58a to 60a and the pipe connecting portions disposed in the individual casings.

The reagent accommodating portion 10 is formed by opening the upper face of the casing 58, and the transparent plates 21 are formed to continue in the horizontal direction when the casings are juxtaposed.

The casing 59 has its front face portion formed of the control panel 23 and the front cover 59b which can be opened/closed in the directions of arrows. The casing 60 has its front face portion formed of the control panel 23 and the front cover 60b, and the casing 58 acting as the reservoir unit has its front face portion formed of the front cover 58b having a large area.

The upper portions of those front face portions are formed such that the aperture 44 of the casing 58 continues to the individual transparent plates 21 which are mounted in the upper portions of the front face portions of the casings 59 and 60. Moreover, the casings 58 to 60 are equipped with the legs 31 on their individual bottom faces.

According to the individual embodiments thus far described, the first passages 58a to 60a are arranged in the front faces so that the piping operation can be facilitated. Moreover, the first passages 58a to 60a can be covered with the covers 11a to 11c having the face portions 20a to 20c, so that the pipes can be shielded. At the same time, the face portions 20a to 20c are formed in the horizontally continuous shape so that the liquid chromatograph body 2 can be given an integral appearance.

In every embodiment of the present invention, the casing are vertically stacked one on another, but the casings may be horizontally juxtaposed one next to another in a similar way. In this case, the passages are provided in the respective upper portions of the casings for communicating with that of another casing when in the juxtaposed state; the covers 11a to 11c are opened upperside of the casing.

As has been detailed above, according to the present invention, it is possible to provide a space-saving-type chromatograph which is enabled to have its component casings either vertically stacked or horizontally juxtaposed and separatedly arranged by giving substantially the same shape to the outer faces of the casings, which can have its reagent feed pipes or the like piped simply at the shortest distance and which has excellent appearance is safe and has an integral exterior.

What is claimed is:

1. A casing structure for a chromatograph comprising:

a plurality of casings, one of said casings containing a separating column, another of said casings containing a sample injector and a third casing containing a detector, wherein said casings can be vertically stacked;

a passage containing eluent feed pipes therein, portions of said passage being located at respective outside portions of each casing, each portion of said passage connecting with another portion of said passage when the casings are stacked, said passage includes an inner hole on the inner side of one of the casings connecting at least one of said eluent feed pipes to at least one of said separating column, said sample injector, and said detector; and a cover at least partially covering the eluent feed pipes accommodated in the passage, said passage being opened towards the outside of the casing when the cover is opened.

2. The casing structure for chromatograph of claim 1, wherein the casing containing the separating column is stacked between the casing containing the sample injector and the casing containing the detector portion.

3. The casing structure for a chromatograph of claim 1 further comprising:

a casing containing a pump unit; and a casing containing an eluent bottle;

the casings containing the sample injector, the separating column and the detector are stacked between the casing containing the pump unit and the casing containing the eluent bottle.

4. The casing structure for a chromatograph of claim 1, wherein each of said casings has plurality of protruding legs on a bottom face thereof and a corresponding number of leg receiving portions recessed in an upper face thereof, whereby said legs of one casing are fitted in said receiving portions on another casing.

5. The casing structure for a chromatograph of claim 1, wherein each of said casings further includes a plurality of notches formed in a least either of two side ends of upper and lower faces thereof.

6. The casing structure for a chromatograph of claim 5, further comprising:

a plurality of fixing plates plugging said notches to fix the lower one of said casings when said casings are stacked, and exposing said notches to the outside to release said lower casing from its fixed state when said casings are separated.

7. The casing structure for a chromatograph of claim 1, wherein each of said casings has a fixing portion in said passage thereof fixing one of said casings to another of said casings.

8. The casing structure for a chromatograph of claim 1, wherein said passages are provided by forming recessed grooves opened towards outside of said casings.

9. The casing structure for a chromatograph of claim 1, wherein each of said casings further includes a cover which is opened towards the outside and is closed from the outside.

10. A casing structure for a chromatograph comprising:

a plurality of casings, one of said casings containing a separating column, another of said casings containing a sample injector and a third casing containing a detector, wherein said casings can be horizontally juxtaposed;

a passage containing eluent feed pipes therein, portions of said passage being located at respective upper portions of each casing, each portion of said passage connecting with another portion of said passage when the casings are in the juxtaposed state, said passage includes an inner hole connecting at least one of said eluent feed pipes to at least one of said separating column, said sample injector and said detector; and a cover at least partially covering the eluent feed pipe accommodated in the passage, said passage being opened towards the upperside of the casing when the cover is opened.

11. The casing structure for a chromatograph of claim 10, wherein the casing containing the separating column is disposed between the casing containing the sample injector and the casing containing the detector.

12. The casing structure for a chromatograph of claim 11, further comprising:

a casing containing a pump unit; and a casing containing an eluent bottle;

the casings containing the sample injector, the separating column and the detector are disposed between the casing containing the pump unit and the casing containing the eluent bottle.

13. The casing structure for a chromatograph of claim 10, wherein said casings have a substantially identical side face shape so that they are horizontally juxtaposed one to another, and include the portions of said passages communicating with one after another when said casings are in the juxtaposed state.

* * * * *

UNITED STATES PATENT AND TRADEMARK OFFICE
CERTIFICATE OF CORRECTION

PATENT NO. : 5,559,283          Page 1 of 2
DATED : 24 September 1996
INVENTOR(S) : Hironori KAJI et al.

It is certified that error appears in the above-identified patent and that said Letters Patent is hereby corrected as shown below:

| Column | Line | |
|---|---|---|
| 1 | 16 | Change "in which" to --comprising--. |
| 1 | 18 | Change "which all" to --all of which--. |
| 2 | 13 | Change "scatter" to --scattering--. |
| 3 | 44 | Change "and are shortened" to --are shortened and--. |
| 4 | 10 | Change "scatter" to --scattering--. |
| 4 | 55 | Change "FIG." to --FIGS.--. |
| 4 | 59 | Change "FIG." to --FIGS.--. |
| 5 | 53 | Change "1e" to --11e--. |
| 8 | 14 | Delete "arranged". |
| 13 | 15 | Delete "each". |

UNITED STATES PATENT AND TRADEMARK OFFICE
CERTIFICATE OF CORRECTION

PATENT NO. : 5,559,283

DATED : September 24, 1996

INVENTOR(S) : Hironori KAJI et al.

It is certified that error appears in the above-identified patent and that said Letters Patent is hereby corrected as shown below:

| Column | Line | |
|---|---|---|
| 13 | 34 | Change "care" to --case--. |
| 13 | 40 | Change "varying" to --variations in--. |
| 17 | 6 | After "appearance" insert --,--. |
| 17 | 48 | Change "a least" to --at least--. |

Signed and Sealed this

Twenty-fifth Day of March, 1997

Attest:

*Attesting Officer*

BRUCE LEHMAN

*Commissioner of Patents and Trademarks*